United States Patent
Kauffmann

(10) Patent No.: US 12,247,989 B2
(45) Date of Patent: Mar. 11, 2025

(54) MULTI-CHANNEL DEVICE FOR CALCULATING COAGULATION CHARACTERISTICS OF A PATIENT'S LIQUID TEST SAMPLE AND METHODS OF USE RELATED THERETO

(71) Applicant: Siemens Healthcare Diagnostics Inc., Tarrytown, NY (US)

(72) Inventor: Aaron Kauffmann, Elkhart, IN (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 1022 days.

(21) Appl. No.: 17/279,890

(22) PCT Filed: Sep. 23, 2019

(86) PCT No.: PCT/US2019/052366
§ 371 (c)(1),
(2) Date: Mar. 25, 2021

(87) PCT Pub. No.: WO2020/068628
PCT Pub. Date: Apr. 2, 2020

(65) Prior Publication Data
US 2022/0034914 A1  Feb. 3, 2022

Related U.S. Application Data

(60) Provisional application No. 62/737,440, filed on Sep. 27, 2018.

(51) Int. Cl.
*G01N 33/86* (2006.01)
*B01L 3/00* (2006.01)
(Continued)

(52) U.S. Cl.
CPC .............. *G01N 33/86* (2013.01); *B01L 3/502* (2013.01); *G01N 21/03* (2013.01); *G01N 21/272* (2013.01);
(Continued)

(58) Field of Classification Search
CPC ...... G01N 33/86; G01N 21/03; G01N 21/272; G01N 21/75; G01N 2021/0325;
(Continued)

(56) References Cited

U.S. PATENT DOCUMENTS 5,039,617 A  8/1991  McDonald et al.
5,110,727 A *  5/1992  Oberhardt ............ G01N 33/525
                                           422/547

(Continued)

FOREIGN PATENT DOCUMENTS

CN  205580983 U  9/2016
EP  1975120 A2  10/2008
WO  8910788 A1  11/1989

OTHER PUBLICATIONS

International Search Report and Written Opinion of International Application No. PCT/US2019/052366 dated Nov. 25, 2019.
European Search Report and Search Opinion of European Patent Application No. 19865144.0 dated Oct. 18, 2021.

*Primary Examiner* — Jill A Warden
*Assistant Examiner* — Alex Ramirez

(57) ABSTRACT

Devices and methods for calculating various coagulation characteristics associated with a patients liquid test sample. The presently disclosed and claimed inventive concept(s) relate to an improved device(s) and method(s) for conducting coagulation assays on a patients liquid test sample, including, without limitation, a patients whole blood sample.

19 Claims, 7 Drawing Sheets

(51) Int. Cl.
  *G01N 21/03* (2006.01)
  *G01N 21/27* (2006.01)
  *G01N 21/75* (2006.01)

(52) U.S. Cl.
  CPC ........ *G01N 21/75* (2013.01); *B01L 2200/025* (2013.01); *B01L 2200/026* (2013.01); *B01L 2200/0684* (2013.01); *B01L 2200/16* (2013.01); *B01L 2300/12* (2013.01); *G01N 2021/0325* (2013.01); *G01N 2021/0346* (2013.01)

(58) Field of Classification Search
  CPC ............. G01N 2021/0346; B01L 3/502; B01L 2200/025; B01L 2200/026; B01L 2200/0684; B01L 2200/16; B01L 2300/12
  See application file for complete search history.

(56) References Cited

U.S. PATENT DOCUMENTS

| | | |
|---|---|---|
| 5,504,011 A | 4/1996 | Gavin et al. |
| 6,077,660 A | 6/2000 | Wong et al. |
| 2004/0191124 A1 | 9/2004 | Noetzel et al. |
| 2006/0110283 A1 | 5/2006 | Fish |
| 2008/0297169 A1 | 12/2008 | Greenquist et al. |
| 2011/0039285 A1 | 2/2011 | Sadaba Champetier De Ribes et al. |
| 2012/0257188 A1* | 10/2012 | Yan ........................ G01N 33/49 356/40 |
| 2017/0122846 A1* | 5/2017 | Holmes ................ G01N 33/491 |

* cited by examiner

MULTI-CHANNEL DEVICE FOR CALCULATING COAGULATION CHARACTERISTICS OF A PATIENT'S LIQUID TEST SAMPLE AND METHODS OF USE RELATED THERETO

CROSS REFERENCE TO RELATED APPLICATIONS

The subject application claims benefit under 35 USC § 119(e) of U.S. provisional Application No. 62/737,440, filed Sep. 27, 2018. The entire contents of the above-referenced patent application are hereby expressly incorporated herein by reference.

STATEMENT REGARDING FEDERALLY FUNDED RESEARCH OR DEVELOPMENT

Not Applicable.

TECHNICAL FIELD

The presently disclosed and claimed inventive concept(s) relate to an improved device(s) and method(s) for conducting coagulation assays on a patient's liquid test sample, including, without limitation, a patient's whole blood sample. More specifically, the presently disclosed and claimed inventive concept(s) relate to a device comprising a plurality of channels for conducting coagulation assay(s) that detect the formation of fibrin within a patient's whole blood sample as measured by, for example, prothrombin time (PT), partial thromboplastin time (PTT), and/or activated partial thromboplastin time (aPTT) associated with such patient's whole blood sample, as well as methods of use related thereto.

BACKGROUND

Numerous devices and methods exist for detecting the level of coagulation of a patient's liquid test sample, such as, by way of example, a patient's whole blood sample. The level of coagulation of a patient's blood sample is diagnostically relevant to not only the overall health of the patient, but, more specifically, it may also be indicative of certain bleeding and/or clotting disorders, including, without limitation, hemophilia A and B, deficiencies in blood-clotting factors (such as, by way of example only, factors II, V, VII, X, and/or XII), and/or Von Willebrand's disease. In addition, measuring the level of coagulation of a patient's blood sample is utilized to determine the effectiveness of certain coagulation and/or anti-coagulation therapies and treatments, such as, by way of example, monitoring the reduction in clotting resulting from the use of heparin and/or other anti-clotting compounds.

The coagulation of a patient's blood sample is accomplished via two distinct, but synergistic pathways—an intrinsic pathway and an extrinsic pathway.

Intrinsic Pathway. The intrinsic pathway cascade is initiated by the activation of factor XII by one or more negatively charged materials and/or molecules, including, without limitation, celite, silica, glass, kaolin, and/or ellagic acid, and/or the proteins kininogen and/or prekallikrein, as well as some fabrics and synthetic plastics. The activated enzyme form of factor XII (factor XIIa) subsequently catalyzes factor XI into activated factor XI (factor XIa) which (in combination with calcium ions) catalyzes the conversion of factor IX into activated factor IX (factor IXa). Factor IXa assembles on the surface of cellular membranes and complexes with factor VIII, the factor IXa-factor VIII complex being stabilized by additional calcium ions. Factor X binds to and is activated by the factor IXa-factor VIII complex thereby forming activated factor X (factor Xa). Factor Xa (along with additional calcium ions) complexes with factor V on cell membrane surfaces, and this factor Xa-factor V complex subsequently binds the blood plasma protein prothrombin and converts the prothrombin into thrombin. Once formed, thrombin associates with and cleaves fibrinogen to form monomeric fibrin, which then link/polymerize to one another to form long fibers that results in clotting/coagulation of the patient's blood sample. Additional bonding of the polymerized fibrin units is promoted by activated factor XIII (factor XIIIa), which stabilizes the clot via formation of cross-linkages.

The activity of the intrinsic coagulation pathway is measured by the PTT, or, if an accelerant and/or activator is added to speed up the clotting time (such as the negatively charged surfaces and/or molecules described hereinabove), by the aPTT. In one common methodology for calculating these intrinsic pathway coagulation charactistics, plasma is collected and anticoagulated with citrate buffer, which binds to and effectively removes functional calcium ions from the plasma. Without the calcium ions, a fibrin clot cannot be generated. Following removal of the calcium ions the plasma is mixed with a negatively charged material(s) and/or molecule(s) to form activated factor XIIa, which then activates factor XI. The intrinsic coagulation pathway is blocked from further activation as a result of the lack of calcium ions, thereby blocking the activation of factor IX. Upon the addition of exogenous calcium ions (and, in some instances, a membrane, such as, by way of example only, a phospholipid membrane, for the assembly of the blood-clotting protein complexes), the duration of time is recorded until a visible clot is formed, the duration of time being the PTT or aPTT, depending on the non-use or use of a clotting accelerant/activator.

Extrinsic Pathway. When tissue cells are injured, coagulation is activated and a fibrin clot is formed. Tissue factor (such, by way of example, thromboplastin) present on the surface(s) of cells is responsible for the initiation of the extrinsic blood coagulation process. Because the pathway of coagulation activated by tissue factor is extrinsic to blood, this process of coagulation is referred to as the extrinsic pathway. In the extrinsic pathway, tissue factor serves as a cofactor with factor VII (or, alternatively, factor IX) that facilitates the activation of factor X. Once activated, Xa (in concert with factor V and calcium ions) proceeds to activate prothrombin to thrombin. As previously discussed, the enzyme thrombin is responsible for converting fibrinogen to monomeric fibrin, which subsequently polymerizes to form blood clots.

The activity of the extrinsic coagulation pathway is measured by the PT. In one common laboratory methodology, tissue is extracted from tissues rich in tissue factor (such as, by way of example, animal tissues). Following extraction, plasma, which, in one instance, has been anticoagulated with a citrate-based buffer, is combined with phospholipid(s), calcium, and thromboplastin. Once these materials are combined, the duration of time until a clot forms is measured, the duration of time being the PT.

Currently, coagulation assays (and the devices that conduct such coagulation assays) are limited to the detection of coagulation and the subsequent calculation of coagulation times (such as, by way of example, PT, PTT, and/or aPTT) via the use of electrochemical and physical motion methodologies. Such methodologies (and devices) include, but are not limited to, detection via the measurement of sample electromagnetic fields and/or light-scattering created by the interrogation of the sample with an optical source(s). Such devices include, but are not limited to, the INRatio® 2 PT/INR Monitoring System commercially offered for sale by Abbott, the Xprecia Stride™ Coagulation Analyzer commercially offered for sale by Siemens Healthcare Diagnostics, Inc., the CoaguChek® Systems commercially offered for sale by Roche, and/or the Coag-Sense® Prothrombin Time (PT)/INR Monitoring System commercially offered for sale by Coag-Sense. In addition, most, if not all, of existing devices require that a patient's liquid test sample be split into subsamples for the conductance of the one or more coagulation assays within the diagnostic devices. This centralized channel for receiving the patient's liquid test sample that connects the various subchannels within the device can result in either cross-contamination or insufficient measurements, as the sample may backflow into the various sub-channels or inadequate volume may enter into a various subchannel(s) for the conductance of the particular diagnostic assay(s).

Accordingly, there is a need for cost-effective, multi-channeled, coagulation assay methodologies and devices that deliver accurate and expedient diagnostic results related to both the intrinsic pathway and extrinsic pathway of coagulation. It is to such devices and methods that the presently disclosed and claimed inventive concept(s) is directed.

DETAILED DESCRIPTION

Figure 1:
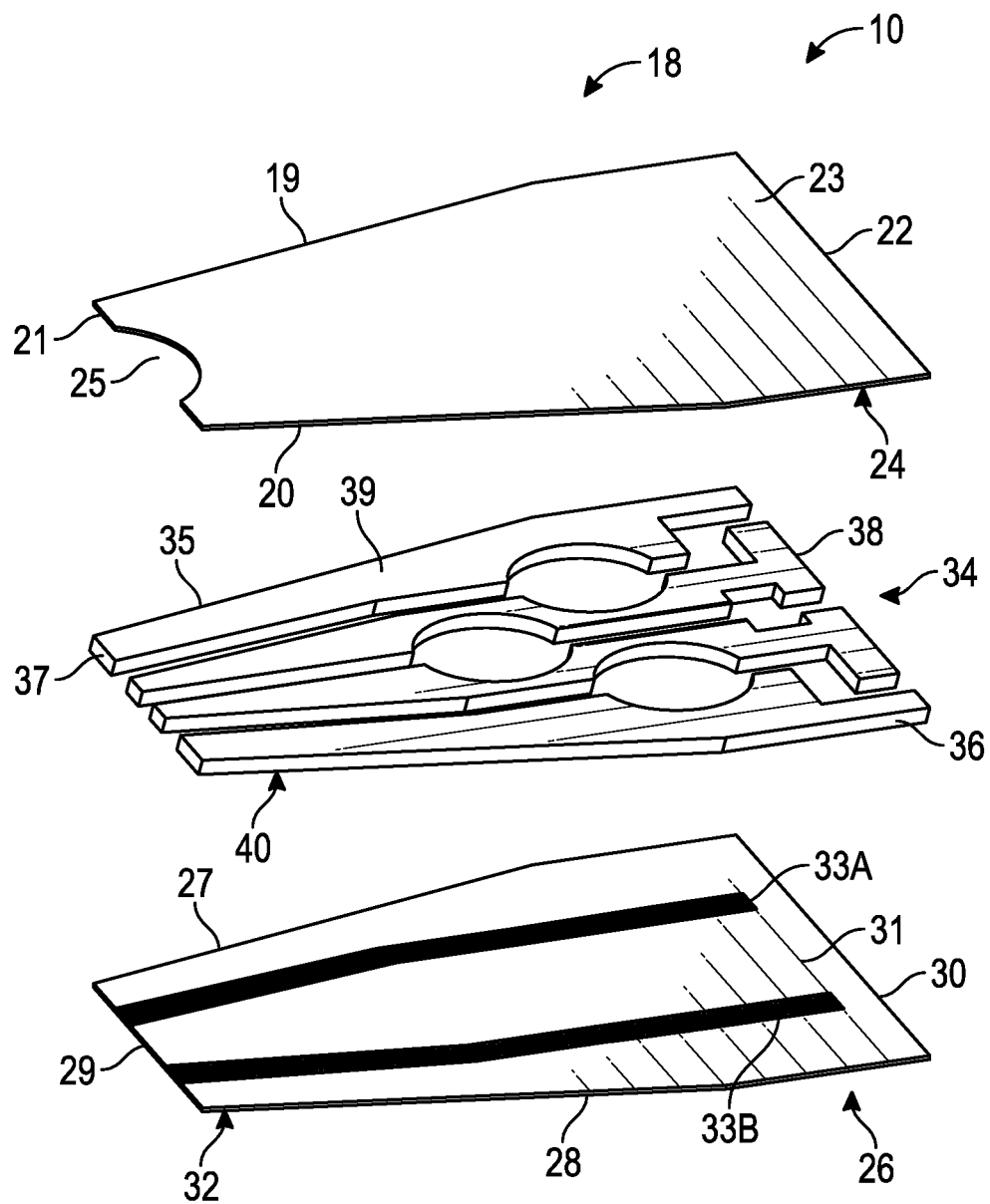
FIG. 1 is an exploded, perspective view of a non-limiting embodiment an improved coagulation assay device constructed in accordance with the presently disclosed and/or claimed inventive concept(s).

Before explaining at least one embodiment of the inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art.

All patents, published patent applications, and non-patent publications mentioned in the specification are indicative of the level of skill of those skilled in the art to which this presently disclosed and claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the devices, kits, and/or methods disclosed and claimed herein can be made and executed without undue experimentation in light of the present disclosure. While the compositions and methods of this presently disclosed and claimed inventive concept(s) have been described in terms of preferred embodiments, it will be apparent to those of skill in the art that variations may be applied to the compositions and/or methods and in the steps or in the sequence of steps of the method described herein without departing from the concept, spirit and scope of the presently disclosed and claimed inventive concept(s). All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The singular forms "a," "an," and "the" include plural referents unless the context clearly indicates otherwise. Thus, for example, reference to "a compound" may refer to 1 or more, 2 or more, 3 or more, 4 or more or greater numbers of compounds. The term "plurality" refers to "two or more." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example but not by way of limitation, when the term "about" is utilized, the designated value may vary by ±20% or ±10%, or ±5%, or ±1%, or ±0.1% from the specified value, as such variations are appropriate to perform the disclosed methods and as understood by persons having ordinary skill in the art. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first", "second", "third", "fourth", etc.) is solely for the purpose of differentiating between two or more items and is not meant to imply any sequence or order or importance to one item over another or any order of addition, for example.

As used in this specification and claim(s), the terms "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein, the phrase "associated with" includes both direct association of two moieties to one another as well as indirect association of two moieties to one another. Non-limiting examples of associations include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety.

The term "liquid test sample" as used herein will be understood to include any type of biological fluid sample that may be utilized in accordance with the presently disclosed and claimed inventive concept(s). Examples of biological samples that may be utilized include, but are not limited to, whole blood or any portion thereof (i.e., plasma or serum), saliva, sputum, cerebrospinal fluid (CSF), intestinal fluid, intraperotineal fluid, cystic fluid, sweat, interstitial fluid, tears, mucus, urine, bladder wash, semen, combinations, and the like. As used herein, the term "volume" as it relates to the liquid test sample utilized in accordance with the presently disclosed and claimed inventive concept(s) means from about 0.1 microliter to about 20 microliters, or from about 0.5 microliter to about 19 microliters, or from about 1 microliter to about 18 microliters, or from about 2 microliters to about 17 microliters, or from about 3 microliters to about 16 microliters, or from about 4 microliters to about 15 microliters, or from about 5 microliters to about 14 microliters, or from about 6 microliters to about 13 microliters, or from about 7 microliters to about 12 microliters, or from about 8 microliters to about 11 microliters, or from about 9 microliters to about 10 microliters. In one non-limiting embodiment of the presently disclosed and/or claimed inventive concept(s), the liquid test sample is a volume of about 15 microliters of either whole blood and/or plasma.

The term "patient" includes human and veterinary subjects. In certain embodiments, a patient is a mammal. In certain other embodiments, the patient is a human. "Mammal" for purposes of treatment refers to any animal classified as a mammal, including human, domestic and farm animals, nonhuman primates, and zoo, sports, or pet animals, such as dogs, horses, cats, cows, etc.

Turning now to particular embodiments, the presently disclosed and claimed inventive concept(s) relate to a multi-channeled device(s) and method(s) for conducting coagulation assays and ascertaining/calculating the various coagulation times associated with a patient's liquid test sample, for instance, by way of example only, a whole blood and/or plasma sample. More specifically, the presently disclosed and claimed inventive concept(s) relate to an improved, multi-channeled coagulation device that comprises a center film which houses the reaction zones and/or optical windows of the improved coagulation device, and methods of use related thereto.

It is contemplated that virtually any reagent used in the fields of biological, chemical, or biochemical analyses and assays could be used in the devices and methods of the presently claimed and disclosed inventive concept(s). It is contemplated that these reagents may undergo physical and/or chemical changes when bound to an analyte of interest whereby the intensity, nature, frequency, or type of signal generated by the reagent-analyte complex is directly proportional or inversely proportional to the concentration of the analyte existing within the fluid sample. These reagents may contain indicator dyes, metal, enzymes, polymers, antibodies, and electrochemically reactive ingredients and/or chemicals that, when reacting with an analyte(s) of interest, may exhibit change in color.

Any method of detecting and measuring the analyte in a fluid sample can be used in the device and methods of the presently claimed and inventive concepts. A variety of assays for detecting analytes are well known in the art and include, but are not limited to, chemical assays, enzyme inhibition assays, antibody stains, latex agglutination, latex agglutination inhibition and immunoassays, such as, radio-immunoassays. The term "antibody" herein is used in the broadest sense and refers to, for example, intact monoclonal antibodies, polyclonal antibodies, multi-specific antibodies (e.g., bispecific antibodies), and to antibody fragments that exhibit the desired biological activity (e.g., antigen/analyte-binding). The antibody can be of any type or class (e.g., IgG, IgE, IgM, IgD, and IgA) or sub-class (e.g., IgG1, IgG2, IgG3, IgG4, IgA1, and IgA2).

While immunoassays (including, but not limited to, sequential analytical chemical and immunoassays) are primarily discussed herein for the detection of at least one analyte of interest present in a liquid test sample, a person having ordinary skill in the art should readily understand that the presently disclosed and claimed inventive concept(s) are not strictly limited to immunoassays and may include, by way of example and not by limitation, chemical and chemical-based assays, nucleic acid assays, lipid-based assays, and serology-based assays. Immunoassays, including radio-immunoassays and enzyme-linked immunoassays, are useful methods for use with the presently claimed and disclosed inventive concepts. A variety of immunoassay formats, including, for example, competitive and non-competitive immunoassay formats, antigen/analyte capture assays and two-antibody sandwich assays can be used in the methods of the invention. Enzyme-linked immunosorbent assays (ELISAs) can be used in the presently claimed and disclosed inventive concepts, as well. In the case of an enzyme immunoassay, an enzyme is typically conjugated to a second antibody, generally by means of glutaraldehyde, periodate, hetero-bifunctional crosslinking agents, or biotin-streptavidin complexes. As will be readily recognized, however, a wide variety of different conjugation techniques exist which are readily available for use with the presently disclosed and claimed inventive concept(s) to one skilled in the art.

Assays, including, but not limited to, light-scattering assays, immunoassays, nucleic acid capture assays, lipid-based assays, and serology-based assays, can be developed for a multiplexed panel of proteins, peptides, and nucleic acids which may be contained within a liquid test sample, with such proteins and peptides including, for example but not by way of limitation, albumin, microalbumin, cholesterol, triglycerides, high-density lipoproteins, low-density lipoproteins, hemoglobin, myoglobin, α-1-microglobin, immunoglobins, enzymes, proteins, glycoproteins, protease inhibitors, drugs, cytokines, creatinine, and glucose. The device(s), kit(s), and method(s) disclosed and/or claimed herein may be used for the analysis of any liquid test sample, including, without limitation, whole blood, serum, and/or plasma.

Referring now to the Figures, and more particularly to FIG. 1, shown therein is a non-limiting embodiment of a multi-channeled coagulation device 10 that conducts coagulation assays and measures the coagulation times associated with a patient's liquid test sample. The coagulation device 10 comprises a top section 18, a bottom section 26, and a center section 34 (which is discussed in greater detail in reference to FIG. 3).

In one non-limiting embodiment, the top section 18 of the coagulation device 10 comprises a first side 19, a second side 20, a first end 21, and a second end 22, a top portion 23, and a bottom portion 24. While shown in FIG. 1 as being substantially rectangular in shape with the top section 18 slightly tapering from the second end 22 to the first end 21, a person having ordinary skill in the art should readily appreciate that the top section 18 (and the overall shape of the device 10) may be any shape capable of accomplishing the presently disclosed and/or claimed inventive concept(s), including, without limitation, circular, triangular, square, rectangular, pentagonal, hexagonal, heptagonal, octagonal, nonagonal, decagonal, and/or any other polygonal shape. In one non-limiting embodiment, the top section 18 of the device 10 is constructed of a transparent film(s) that ranged in thickness from about 0.1 millimeter to about 1 millimeter, or from about 0.2 millimeter to about 0.9 millimeter, or from about 0.3 millimeter to about 0.8 millimeter, or from about 0.4 millimeter to about 0.7 millimeter, or from about 0.5 millimeter to about 0.6 millimeter. The transparent film(s) mitigate light scatter when an optical source, including, without limitation, a spectrophotometer, fluorometer, and/or nephelometer interrogates one or more of the optical windows of the center section 34 containing a patient's liquid test sample and coagulation reagents (discussed in further detail with respect to FIG. 3). In one non-limiting embodiment, the transparent film(s) may comprise or consist of acrylic, polystyrene, styrene-acrylonitrile, polycarbonate, polyethylene terephthalate, and combinations thereof.

Figure 3:
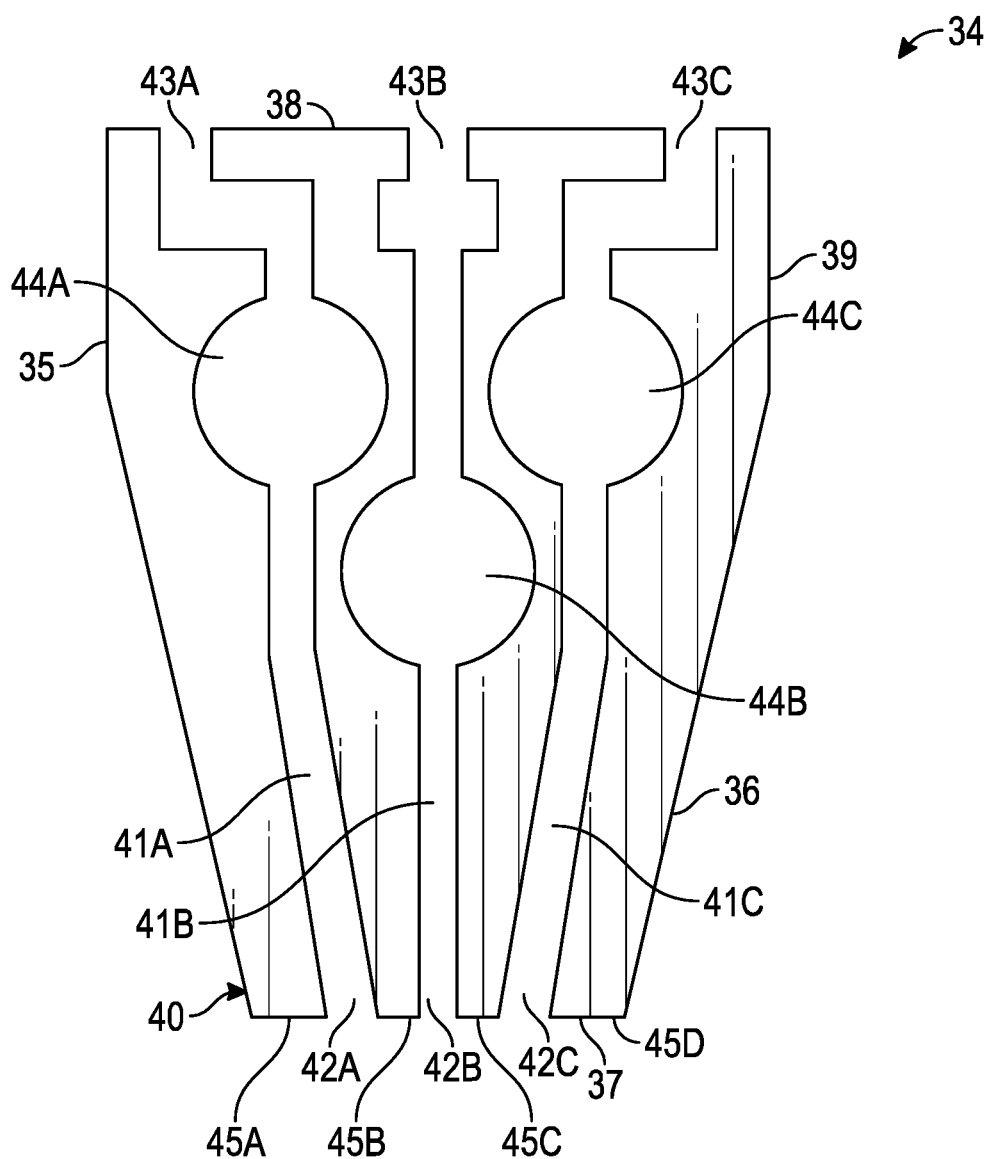
FIG. 3 is a detailed view of a non-limiting embodiment of a center section of an improved coagulation assay device constructed in accordance with the presently disclosed and/or claimed inventive concept(s).

In one non-limiting embodiment, the top section 18 comprises a sample receptacle 25 for receiving a sample holder (not shown) that contains the patient's liquid test sample which is in fluid communication with each channel of the plurality of channels of the center portion 34 (discussed in greater detail herein with respect to FIG. 3). Once inserted into the sample receptacle 25 (as shown in greater detail in FIG. 4A), the patient's liquid test sample diffuses (for instance, via capillary action) from the sample holder into the capillaries of the center section 34 into the sample window(s) for conductance of one or more coagulation assay(s) and measurement(s). In one non-limiting embodiment, and as shown in FIG. 1, the sample receptacle 25 is located at the first end 21 of the top section 18 substantially between the first side 19 and second side 20. While shown in FIG. 1 as being substantially semi-circle in shape, a person having ordinary skill in the art should readily appreciate that the sample receptacle 25 is not limited to this shape and may be any shape capable of accomplishing the presently disclosed and/or claimed inventive concept(s). In addition, while shown as being located at (or near) the first end 21 substantially between the first side 19 and second side 20 of the top section 18, the sample receptacle 25 may be located at any location on the coagulation device 10 capable of accomplishing the presently disclosed and/or claimed inventive concept(s), including without limitation, (1) at any location on the on the top section 18; (2) at any location on the bottom section 26; (3) at or near a first end 29 (described elsewhere herein) of the bottom section 26; (4) at any location on the first side 19, the second side 20, or the second end 22 of the top section 18; (5) at or near a first end 37 of a center section 34 (discussed elsewhere herein)' and/or (6) at any location along a first side 35 and/or a second side 36 of the center section 34.

In one non-limiting embodiment, the bottom section 26 comprises a first side 27, a second side 28, a first end 29, a second end 30, a top portion 31, and a bottom portion 32. While shown in FIG. 1 as being substantially rectangular in shape with the bottom section 26 slightly tapering from the second end 30 to the first end 29, a person having ordinary skill in the art should readily appreciate that the top section 18 (and the overall shape of the device 10) may be any shape capable of accomplishing the presently disclosed and/or claimed inventive concept(s), including, without limitation, circular, triangular, square, rectangular, pentagonal, hexagonal, heptagonal, octagonal, nonagonal, decagonal, and/or any other polygonal shape. In one non-limiting embodiment, the bottom section 26 of the device 10 is constructed of a transparent film(s) that ranged in thickness from about 0.1 millimeter to about 1 millimeter, or from about 0.2 millimeter to about 0.9 millimeter, or from about 0.3 millimeter to about 0.8 millimeter, or from about 0.4 millimeter to about 0.7 millimeter, or from about 0.5 millimeter to about 0.6 millimeter. The transparent film(s) mitigate light scatter when an optical source, including, without limitation, a spectrophotometer, interrogates one or more of the optical windows of the center section 34 containing a patient's liquid test sample and coagulation reagents (discussed in further detail with respect to FIG. 3). In one non-limiting embodiment, the transparent film(s) may comprise or consist of acrylic, polystyrene, styrene-acrylonitrile, polycarbonate, polyethylene terephthalate, and combinations thereof.

In non-limiting embodiment and as shown in FIG. 1, the bottom section 26 further comprises a plurality of areas comprising at least one coagulation reagent. As shown in FIG. 1, the plurality of areas comprising at least one coagulation reagent may be organized in strips, for instance coagulation reagent strips 33A and 33B, located on the top portion 31 of the bottom section 26 extending longitudinally between the first end 29 and the second end 30 of the bottom section 26. In this embodiment, when the bottom section 26 is overlaid with the center section 34, at least a portion of the coagulation reagent strips 33A and 33B are disposed within any combination of the optical windows (identified in FIG. 3 as reference numerals 44A, 44B, and 44C) for the conductance of coagulation assay(s) upon the patient's liquid test sample coming into contact with the portion of coagulation strips 33A and 33B disposed within the combination of optical windows to form a reacted sample. Alternatively, rather than strips on the top portion 31 running substantially parallel to one another and longitudinally from the first end 29 to the second end 30, the coagulation reagents may be individually deposited within the combination of optical windows for the conductance of coagulation assay(s).

Figure 2:
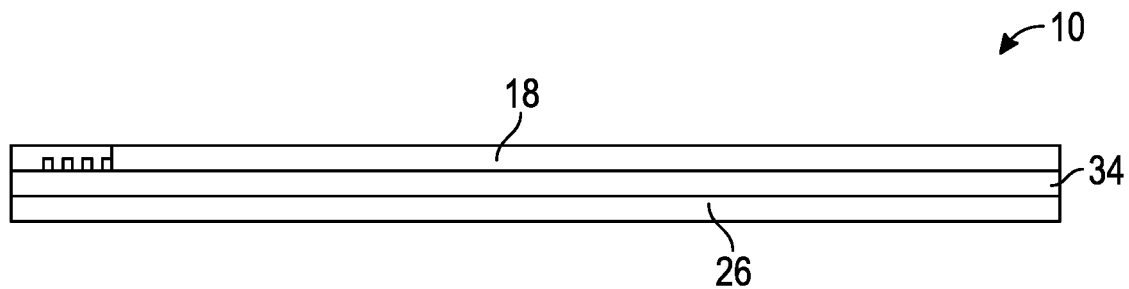
FIG. 2 is a side view of the improved coagulation assay device of FIG. 1.

In one non-limiting embodiment, the center section 34 comprises a first side 35, a second side 36, a first end 37, a second end 38, a top portion 39, and bottom portion 40. As shown in FIGS. 1 and 2, the center section 34 is disposed between (i.e., sandwiched) the top section 18 and the bottom section 26 in accordance with the presently disclosed and/or claimed inventive concept(s). The top portion 38 of the center section 34 is adhered (for instance, via any non-reactive adhesive commonly known in the art) to the bottom portion 24 of the top section 18 while the bottom portion 40 of the center section 34 is adhered to the top portion 31 of the bottom section 26 to form the device 10. There is no need for the entirety of the center section 34 to be transparent; rather only the optical windows (shown in FIG. 3) need to be transparent in order to mitigate the scattering of light resulting from optical interrogation of the reacted sample(s) (i.e., the patient's liquid test sample combined with one or more coagulation reagents).

Referring now to FIG. 3, shown therein is a detailed view of a non-limiting embodiment of a center section 34 of the improved coagulation assay device 10. The center section 34 shown in FIG. 3 is substantially identical both in construction and function(s) to the center section 34 previously discussed with respect to FIG. 1. Accordingly, only the additional features of the center section 34 not discussed with respect to FIG. 1 will be discussed with respect to FIG. 3.

As shown in FIG. 3, the center section 34 comprises a plurality of channels (such as microchannels or capillaries), including, without a limitation, a first channel 41A, a second channel 41B, and a third channel 41C. While shown in FIG. 3 as comprising three separate channels, a person having ordinary skill in the art should readily appreciate that the center section 34 may comprise and/or consist of any number of channels capable of accomplishing the presently disclosed and/or claimed inventive concept(s), including, without limitation, 2, 3, 4, 5, 6, 7, 8, 9, or greater than or equal to 10 channels. In one non-limiting embodiment and as shown in FIG. 3, each channel of the plurality of channels extends substantially longitudinally between the first end 37 and the second end 38, and parallel to the first side 35 and second side 36 of the center portion 34; however, a person having ordinary skill in the art should readily appreciate that each channel of the plurality of channels may be oriented in any direction capable of accomplishing the presently disclosed and/or claimed inventive concept(s).

Each channel of the plurality of channels comprises an opening, for instance, by way of example, the first channel 41A comprises a first opening 42A, the second channel 41B comprises a second opening 42B, and the third channel 41C comprises a third opening 42C. The openings receive the patient's diffused liquid test sample from the sample receptacle 25 of the top portion 18 (once the sample holder has been inserted and received by the sample receptacle 25). Once received, the patient's liquid test sample diffuses from the openings (for instance, via capillary action) into the plurality of channels and travels toward the particular channel's optical window (discussed in greater detail hereinbelow). Each opening of the plurality of openings (and or each capillary) comprises a width, for example, of about 0.1 millimeter to about 1 millimeter, or from about 0.2 millimeter to about 0.9 millimeter, or from about 0.3 millimeter to about 0.8 millimeter, or from about 0.4 millimeter to about 0.7 millimeter, or from about 0.5 millimeter to about 0.6 millimeter. In one non-limiting embodiment, the width of each opening (and respective channel) is about 0.4 millimeter. While shown as being disposed at the first end 37 of the center section 34, each opening of the plurality of openings may be disposed at any position (including different positions) of the center section 34 capable of accomplishing the presently disclosed and/or claimed inventive concept(s).

In one non-limiting embodiment, each channel of the plurality of channels comprises a vent, for instance, by way of example, the first channel 41A comprises a first vent 43A, the second channel 41B comprises a second vent 43B, and the third channel 41C comprises a third vent 43C. The vents facilitate the capillary action that allows for the diffusion of the patient's liquid test sample through the respective opening(s) into the respective channel(s) and to the respective sample window(s) for the conductance of at least one coagulation assay.

In one non-limiting embodiment, the center portion 34 comprises a plurality of spacers, for instance, by way of example only, a first spacer 45A, a second spacer 45B, a third spacer 45C, and a fourth spacer 45D, that separate the channels from one another. The number of spacers is dependent on the number of channels comprising the center portion 34 of the coagulation device 10. For instance, and as shown in FIG. 3, the center portion may comprise four spacers when the center portion 34 comprises and/or consists of three channels. The spacers ensure that the patient's liquid test sample remains in the respective channels while simultaneously ensuring that the channels never cross, which eliminates assay cross-contamination between the channels.

In one non-limiting embodiment, each channel of the plurality of channels comprises an optical window, for instance, by way of example only, the first channel 41A comprises a first optical window 44A, the second channel 41B comprises a second optical window 44B, and the third channel 41C comprises a third optical window 44C. Each optical window of the plurality of optical windows is disposed between its respective channel's opening and vent. For instance, by way of example only, the first optical window 44A is disposed between the first opening 42A and the first vent 43A of the first channel 41A. In the currently disclosed and/or claimed inventive concept(s), each channel of the center section 34 comprises its own opening, vent, and optical window.

While described with respect to a single channel, the below recited methodology and structure(s) are applicable to all channels of the center portion 34 of the improved coagulation device 10. Once a channel receives the patient's liquid test sample, for instance, via diffusion into the capillary from the sample receptacle 25 of the top section 18, the patient's liquid test sample diffuses (i.e., via capillary action) from the opening of the capillary and a volume of the patient's liquid test sample enters and fills or partially fills the optical window. Once entering the optical window (as shown in greater detail with respect to FIGS. 4A and 4B), the patient's liquid test sample mixes with the various coagulation assay reagent(s) disposed or contained within the optical window to thereby being a coagulation process. After mixing, the reacted sample within the optical window is interrogated by an optical source (for instance, by way of example only, an optical light source at a specific wavelength emitted from a spectrophotometer, fluorometer, or nephelometer) to measure the absorbance of the reacted sample or the change in absorbance of the reacted sample over a period of time. In one non-limiting embodiment, the specific wavelength is in the far-red region of light (i.e., from about 750 nanometers to about 850 nanometers) and such wavelength of light is emitted by a nephelometer.

Figure 4A:
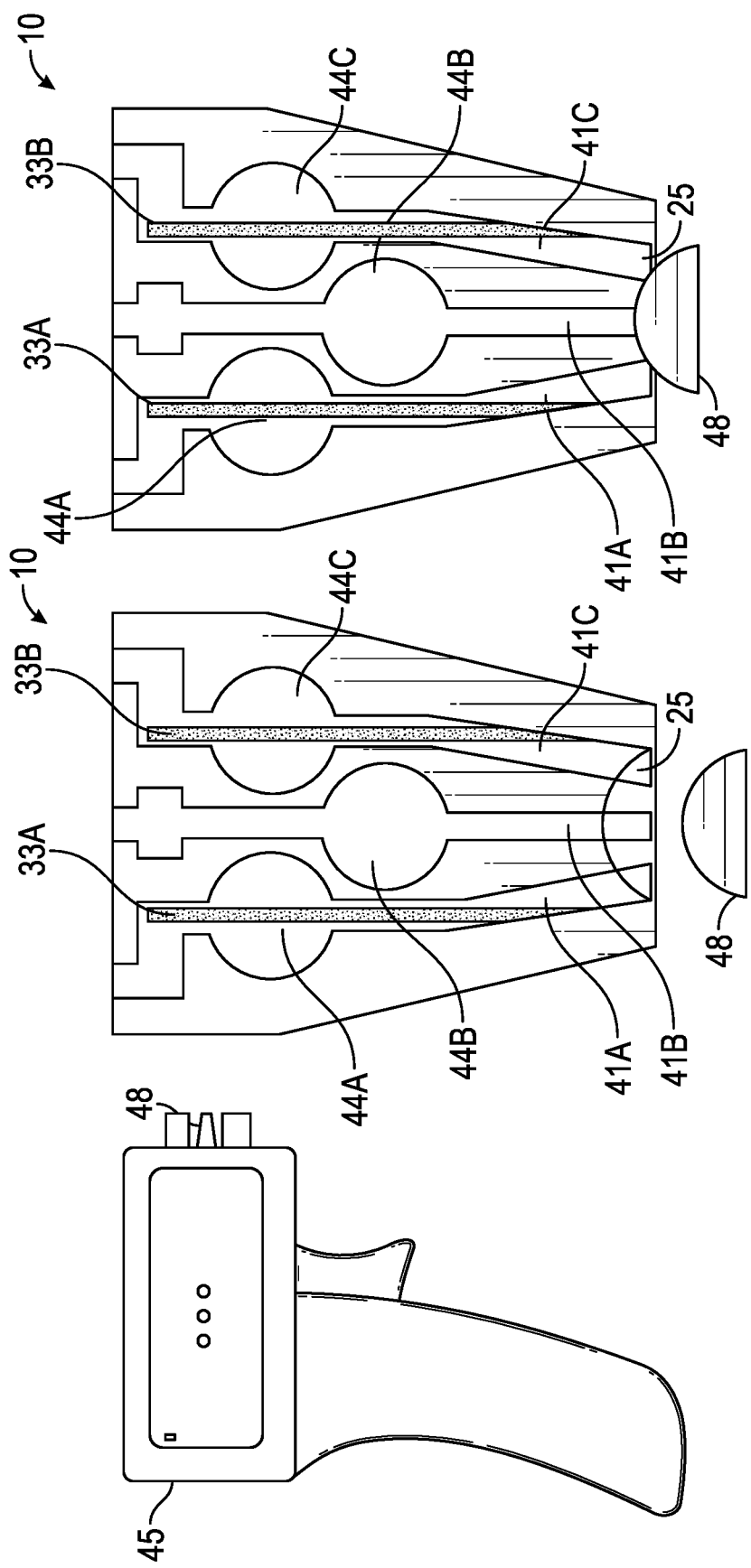
FIGS. 4A and 4B is a detailed view of a non-limiting embodiment of a method for conducting at least one coagulation assay utilizing the improved coagulation device in accordance with the presently disclosed and/or claimed inventive concept(s).
Figure 4B:
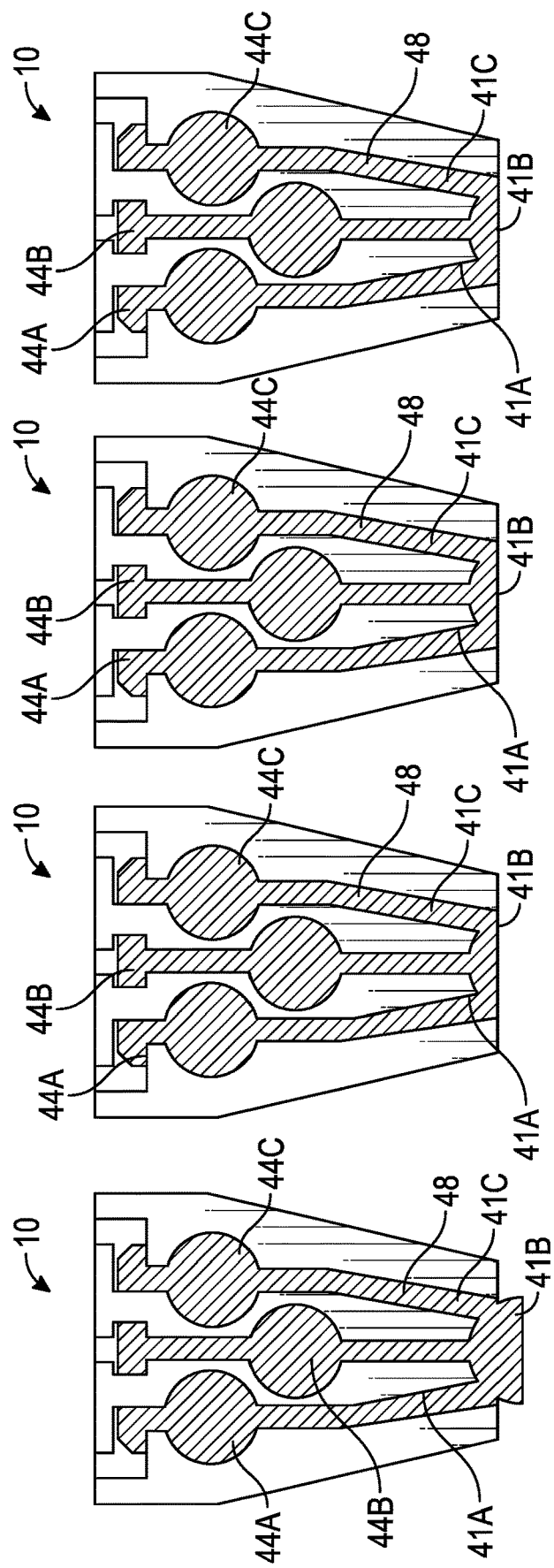

Referring now to FIGS. 4A and 4B, is a detailed view of a non-limiting embodiment of a method for conducting at least one coagulation assay (and determining various coagulation assay measurements, such as PT, PTT, and/or aPTT) utilizing the improved coagulation device 10 in accordance with the presently disclosed and/or claimed inventive concept(s). The description(s) of the improved coagulation device 10, as well as the descriptions with respect to the top section 18, the bottom section 26, and center section 34 of the coagulation device 10, herein are deemed wholly relevant to the description of the methodology depicted in FIGS. 4A and 4B. Moreover, the improved coagulation device 10 may combined with or inserted into an analyzer for the conductance of the measurements associated with the various coagulation assays.

A patient's liquid test sample 48 is first collected (for instance, via a handheld finger stick collection device 45). Once collected, the patient's liquid test sample 48 is introduced into the coagulation device 10 via insertion into the sample receptacle 25 of the top section 18 of which is in fluid communication with each of the channels comprising the plurality of channels the central section 34, including, without limitation, the first channel 41A, the second channel 41B, and the third channel 41C. Following insertion of the patient's liquid test sample (for instance, a whole blood sample) into the sample receptacle 25, the sample diffuses (i.e., via capillary action) into each of the channels comprising the plurality of channels and further diffuses (via capillary action) through each of the channels into the respective optical window (for instance, by way of example, the first optical window 44A, the second optical window 44B, and/or the third optical window 44C, where it mixes with at least one coagulation assay reagent to form a reacted sample. Once the reacted sample is formed, each of the optical windows of the plurality of optical windows is interrogated by an optical source at a specific wavelength or a range of wavelengths (for instance, wavelengths within the far-red spectrum). Thereafter, various coagulation measurements, for instance, by way of example only, nephelometric and/or turbidimetric measurements, over a specific, predetermined intervals and duration of time are taken of the reacted sample to thereby establish various coagulation characteristics of the patient's liquid test sample, including, without limitation, the PT, PTT, and/or aPTT associated with the reacted sample.

Experimental Data.

Figure 5:
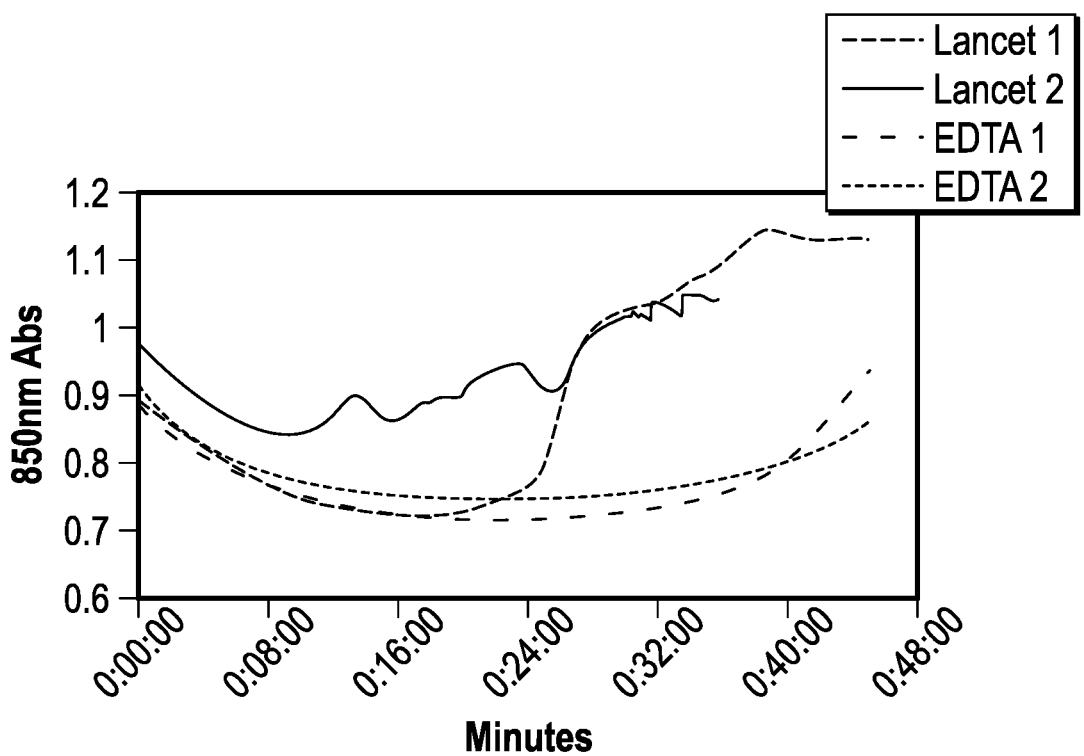
FIG. 5 is a graphical representation of the raw absorbance data collected for two lancet samples and two EDTA coagulation control samples measured as absorbance at 850 nanometers versus time of coagulation.

Referring now to FIG. 5, shown therein is a graphical representation of the raw absorbance data collected for two samples and two controls measured as absorbance at 850 nanometers versus time of coagulation. As the data was collected, all of the 850 nanometer-absorbance reading followed a parabolic path. These paths are due to the hemolysis, evaporation concentrating, non-specific hemoglobin agglutination, or any combination thereof. The peaks seen in the two lancet datasets represent coagulation as they are absent from the two ethylenediaminetetraacetic acid (EDTA) coagulation control samples. No accelerant, such as, by way of example only, thromboplastin or celite, silica, kaolin, and/or ellagic acid was added to the two lancet samples, so coagulation of these samples resulted in the standard about 8 minute- to about 16 minute-range rather than a standard point-of-care coagulation assay time range of about 30 seconds to about 4 minutes.

The shape of the EDTA coagulation control samples are due to hemolysis in the beginning of the coagulation assay decreasing the absorbance signal and then the samples evaporating thereby concentrating the samples. The rate of hemolysis is decreasing with time as the samples reach an ionic/pH equilibrium from the intracellular fluid released.

As shown in FIG. 5, the data for lancet sample 1 was collected on day 1 from a fresh finger stick (~10 seconds to first read), read at 850 nanometers every 6 seconds at a temperature of about 25° C. The channel of the improved coagulation device constructed in accordance with the presently disclosed and/or claimed inventive concept(s) containing lancet sample 1 comprises a volume threshold of about 15 microliters, while the optical window comprises a volume threshold of about 6 microliters. With respect to FIG. 5, the path length of the lancet sample 1 is about 0.4 millimeters with a channel diameter of about 4.75 millimeters.

The data for lancet sample 2 was collected on day 3 from the fresh finger stick following the same parameters as lancet sample 1.

The EDTA coagulation control samples 1 and 2 datasets were collected on day 2 from an intravenous blood draw stored in EDTA anticoagulant.

Figure 6:
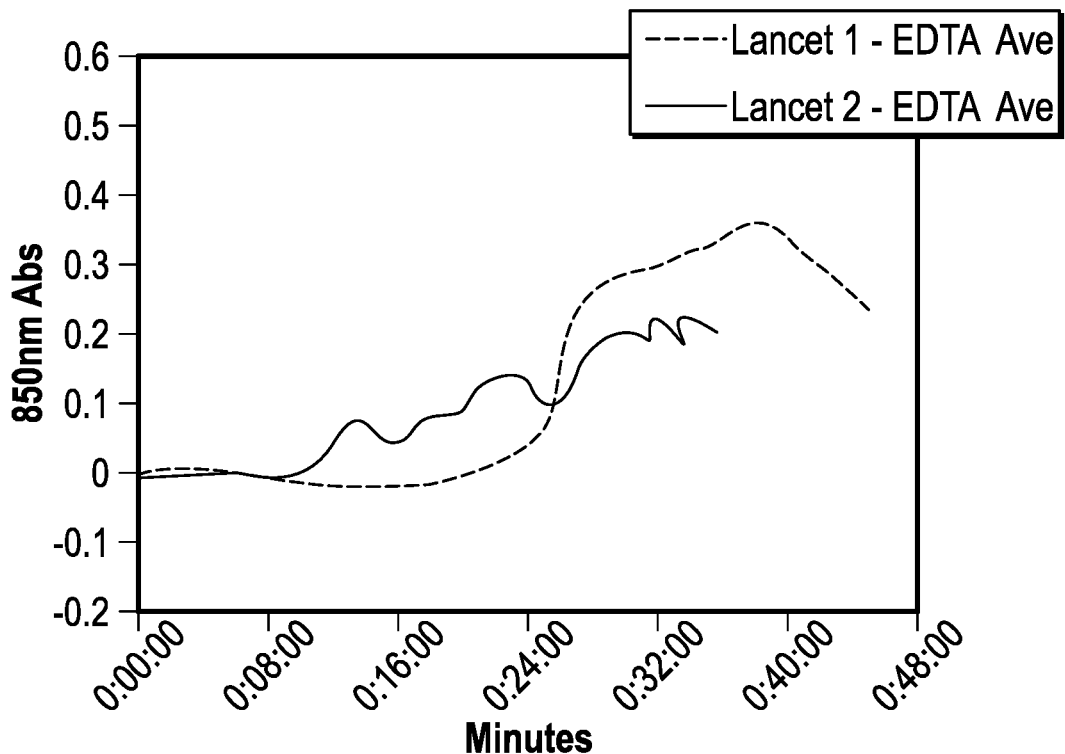
FIG. 6 is a graphical representation of the raw absorbance data collected for the two lancet samples of FIG. 5 which have been signal corrected by reference subtraction in accordance with the presently disclosed and/or claimed inventive concept(s).

Referring now to FIG. 6, shown therein is a graphical representation of the raw absorbance data collected for the two lancet samples of FIG. 5 which have been signal corrected by reference subtraction in accordance with the presently disclosed and/or claimed inventive concept(s). In order to correct the absorbance signals of each of the lancet samples 1 and 2 in order to yield a more detailed analysis of the coagulation times associated with the samples, the average absorbance value of the EDTA coagulation control samples 1 and 2 (shown in FIG. 5) is calculated and then subtracted from the absorbances of each of the lancet samples 1 and 2. As shown in FIG. 6, the values plotted therein represent the absorbance values of lancet samples 1 and 2 with the corresponding absorbance value average of EDTA coagulation controls samples 1 and 2 subtracted therefrom at the equivalent $T_{minute}$.

Figure 7:
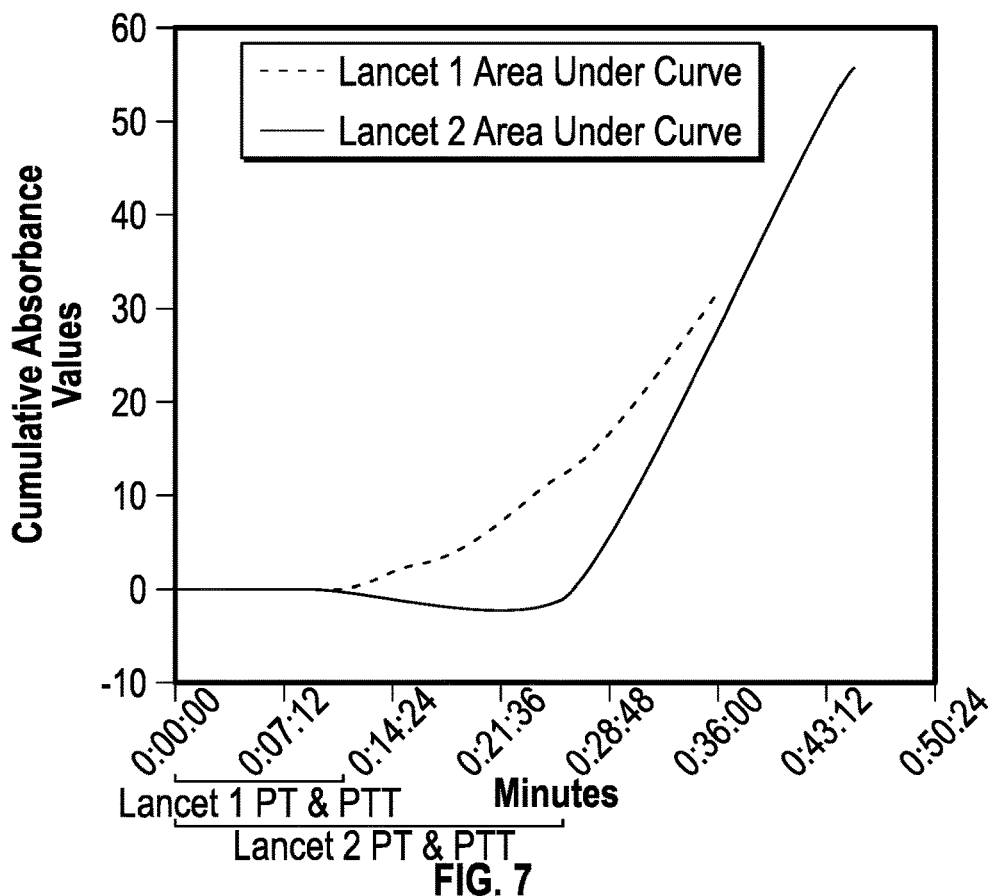
FIG. 7 is a graphical representation of the PT and aPTT associated with the two lancet samples of FIG. 6 in accordance with the presently disclosed and/or claimed inventive concept(s).

Referring now to FIG. 7, shown therein is a graphical representation of the PT and aPTT associated with the two lancet samples of FIG. 6 in accordance with the presently disclosed and/or claimed inventive concept(s). In FIG. 7, the cumulative absorbance values of each of lancet samples 1 and 2 are plotted against time (in minutes). When adding the absorbance values for a plot area under each curve of lancet 1 and lancet 2 (as shown in FIG. 6), an inflection point is obtained, subsequently followed by absorbance increases due to fibrin formation (i.e., clotting). Accordingly, depending on the reagents used, the PT and/or PTT/aPTT is calculated for each lancet sample 1 and 2 (which is the time, in minutes, at which time the cumulative absorbance time of each sample begins to increase due to the fibrin formation). As no reagents were used to accelerate fibrin formation in either lancet sample 1 or 2, clotting time (i.e., PT or PTT) was about 8 minutes for lancet sample 1 and about 16 minutes for lancet sample 2.

Figure 8:
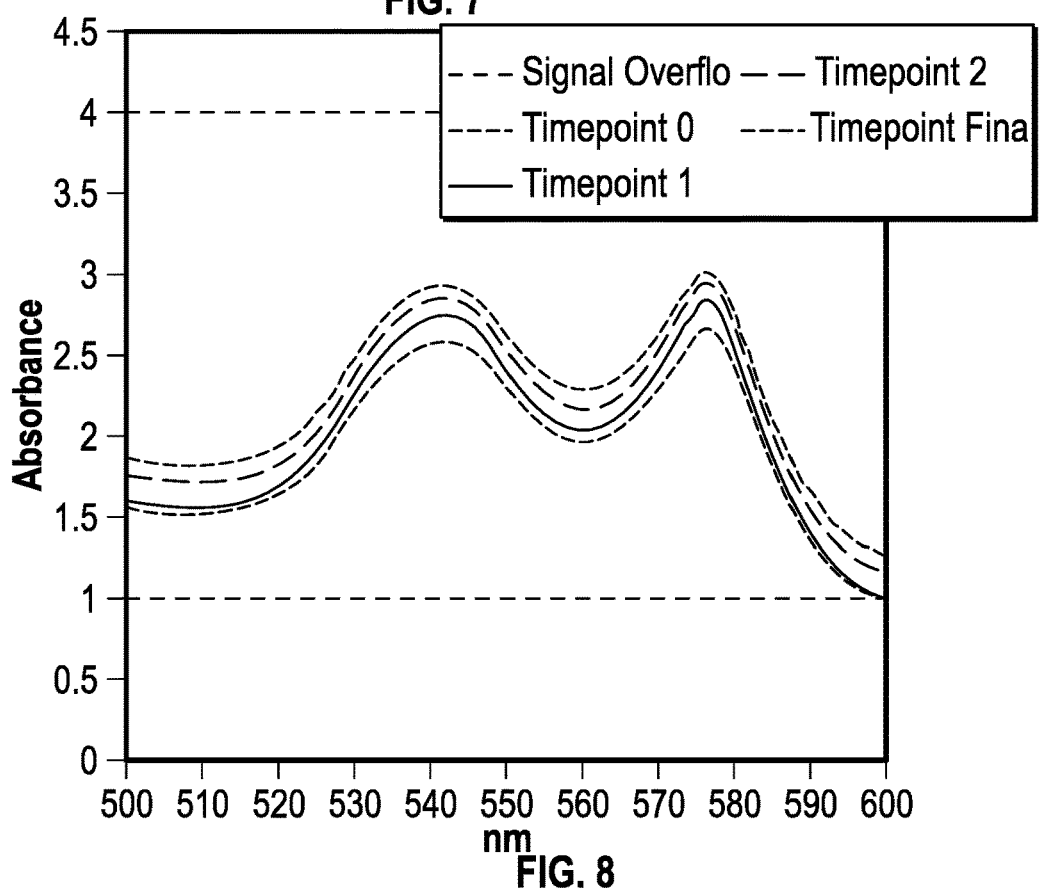
FIG. 8 is a graphical representation of a single whole blood sample collected in accordance with the presently disclosed and/or claimed inventive concept(s) in which the absorbance of the sample is measured against a wavelength spectrum ranging from 500 nanometers to 600 nanometers.

Referring now to FIG. 8, shown therein is a graphical representation of a single whole blood sample collected in accordance with the presently disclosed and/or claimed inventive concept(s) in which the absorbance of the sample is measured against a wavelength spectrum ranging from 500 nanometers to 600 nanometers. FIG. 6 shows the impact that times has on the spectra of whole blood sample. A finger stick, whole blood sample was taken and the absorbance spectra of the sample was collected every 5-7 minutes in a spectrum ranging from 300 nanometers to 1,000 nanometers. FIG. 6 depicts why it is not advantageous to measure sample absorbance for coagulation at wavelengths below the far-red region (from about 700 nanometers to about 850 nanometers). In the 500 nanometer- to 600 nanometer-spectrum, for instance and as shown in FIG. 6, regions of non-linearity are observed, but these regions of non-linearity are due to concentration of hemoglobin within the whole blood sample, rather than to the initiation of clotting.

Figure 9:
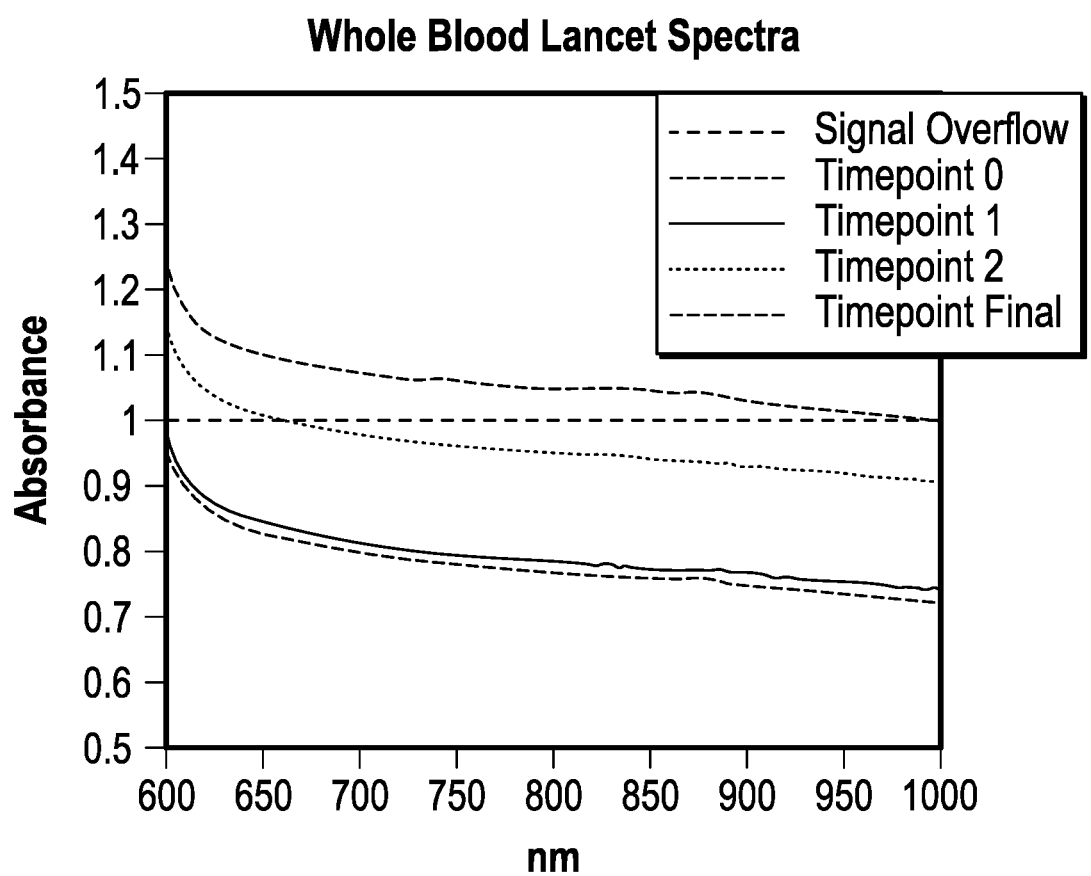
FIG. 9 is a graphical representation of the same single whole blood sample of FIG. 8 in which the measurements are shifted to show such absorbance over the entire wavelength spectrum ranging from 600 nanometers to 1,000 nanometers.

Referring now to FIG. 9, shown therein is a graphical representation of the same single whole blood sample of FIG. 8 in which the measurements are shifted to show such absorbance over the entire wavelength spectrum ranging from 600 nanometers to 1,000 nanometers. The spectrum for hemoglobin alone does not show substantial absorbance at wavelengths equal to or greater than about 750 nanometers. As shown in FIG. 9, the absorbance readings in the about 750 nanometer- to 1,000 nanometer-range are reading absorbances associated with larger objects, such as intact red blood cells, clusters of red blood cells, and/or fibrin complexes. At timepoint 2 and timepoint final, it is clear that clotting has been initiated and that absorbance is increasing.

NON-LIMITING EXAMPLES OF THE INVENTIVE CONCEPT(S)

A coagulation device for the conductance of at least one coagulation assay on a patient's liquid test sample, comprising: a top section, the top section comprising at least one side, a top portion, and a bottom portion; a bottom section, the bottom section comprising at least one side, a top portion, and a bottom portion; a center section, the center section comprising at least one side, a top portion, and a bottom portion, the center section being disposed between the top section and the bottom section, the center section further comprising at least two channels, wherein each of the at least two channels comprises an opening in fluid communication with a sample receptacle for receiving a patient's liquid test sample, further wherein each of the at least two channels is open to the top portion of the bottom section and each of the at least two channels comprises a sample window containing at least one coagulation assay reagent for conducting at least one coagulation assay, the center section further comprising at least one spacer that completely separates each of the at least two channels from one another.

The coagulation device, wherein the patient's liquid test sample is selected from the group consisting of whole blood, plasma, and combinations thereof.

The coagulation device, wherein the patient's liquid test sample comprises a volume of about 15 microliters.

The coagulation device, wherein the top section, bottom section, and center section are constructed of materials selected from the group consisting of acrylic, polystyrene, styrene-acrylonitrile, polycarbonate, polyethylene terephthalate, and combinations thereof.

The coagulation device, wherein each of the at least two channels further comprises a vent.

The coagulation device, wherein the top portion of the bottom section comprises the at least one coagulation assay reagent.

The coagulation device, wherein the at least one coagulation assay reagent is selected from the group consisting of thrombopastin, celite, silica, glass, kaolin, ellagic acid, kininogen, prekallikrein, fabric, synthetic plastic, and combination thereof.

The coagulation device, wherein the at least one coagulation assay is measured by optical interrogation at a specific wavelength by an optical source.

The coagulation device, wherein the optical source is selected from the group consisting of a spectrophotometer, fluorometer, and nephelometer.

The coagulation device, wherein the specific wavelength is selected from a range of wavelengths selected from the group consisting of 750 nanometers to 850 nanometers.

A method for measuring the coagulation characteristics associated with a patient's liquid test sample, the method comprising the steps of: obtaining a patient's liquid test sample; introducing the patient's liquid test sample into a coagulation device, the coagulation device comprising: a top section, the top section comprising at least one side, a top portion, and a bottom portion; a bottom section, the bottom section comprising at least one side, a top portion, and a bottom portion; a center section, the center section comprising at least one side, a top portion, and a bottom portion, the center section being disposed between the top section and the bottom section, the center section further comprising at least two channels, wherein each of the at least two channels comprises an opening in fluid communication with a sample receptacle that receives a patient's liquid test sample upon introduction into the coagulation device, further wherein each of the at least two channels is open to the top portion of the bottom section and each of the at least two channels comprises a sample window containing at least one coagulation assay reagent for conducting at least one coagulation assay, the center section further comprising at least one spacer that completely separates each of the at least two channels from one another; reacting the patient's liquid test sample with the at least one coagulation assay reagent within each sample window of each of the at least two channels to thereby form a reacted sample; interrogating the reacted sample within each optical window with a specific wavelength of light emitted from an optical source, the interrogation occurring over a particular duration of time at predetermined intervals; measuring the reacted sample to determine a plurality of coagulation characteristics associated with the reacted sample.

The method, wherein the patient's liquid test sample is selected from the group consisting of whole blood, plasma, and combinations thereof.

The method, wherein the patient's liquid test sample comprises a volume of about 15 microliters.

The method, wherein the top section, bottom section, and center section of the coagulation device are constructed of materials selected from the group consisting of acrylic, polystyrene, styrene-acrylonitrile, polycarbonate, polyethylene terephthalate, and combinations thereof.

The method, wherein each of the at least two channels of the center section further comprises a vent.

The method, wherein the top portion of the bottom section comprises the at least one coagulation assay reagent.

The method, wherein the at least one coagulation assay reagent is selected from the group consisting of thrombopastin, celite, silica, glass, kaolin, ellagic acid, kininogen, prekallikrein, fabric, synthetic plastic, and combination thereof.

The method, the optical source is selected from the group consisting of a spectrophotometer, fluorometer, and nephelometer.

The method, the specific wavelength is selected from a range of wavelengths selected from the group consisting of 750 nanometers to 850 nanometers.

The method, wherein the plurality of coagulation characteristics associated with the reacted sample is selected from the group consisting of PT, PTT, aPTT, and combinations thereof.

Thus, in accordance with the presently disclosed and claimed inventive concept(s), there have been provided devices and methods for measuring the coagulation characteristics of a patient's liquid test sample. As described herein, the presently disclosed and claimed inventive concept(s) relate to embodiments of an improved multi-channeled coagulation device for use in the detection and measurement of coagulation assay characteristics (such as, by way of example only, PT, PTT, and/or aPTT) associated with a patient's liquid test sample (for instance, by way of example, a patient's whole blood and/or serum sample). Such presently disclosed and/or claimed inventive concept(s) fully satisfy the objectives and advantages set forth hereinabove. Although the presently disclosed and claimed inventive concept(s) has been described in conjunction with the specific drawings, experimentation, results, and language set forth hereinabove, it is evident that many alternatives, modifications, and variations will be apparent to those skilled in the art. Accordingly, it is intended to embrace all such alternatives, modifications, and variations that fall within the spirit and broad scope of the presently disclosed and claimed inventive concept(s).

What is claimed is:

1. A coagulation device for the conductance of coagulation assays on a patient's liquid test sample to determine a plurality of coagulation characteristics associated with intrinsic and extrinsic pathways of coagulation, the coagulation device comprising:
   a top section, the top section comprising at least one side, a top portion, a bottom portion, and a sample receptacle;
   a bottom section, the bottom section comprising at least one side, a top portion, and a bottom portion;
   a center section, the center section comprising at least one side, a top portion, and a bottom portion, the center section being disposed between the top section and the bottom section, the center section further comprising at least two channels, wherein each of the at least two channels comprises an opening in fluid communication with the sample receptacle for receiving a patient's liquid test sample, further wherein each of the at least two channels is open to the top portion of the bottom section and each of the at least two channels comprises a sample window containing at least one coagulation assay reagent for conducting at least one coagulation assay in each of the at least two channels, the center section further comprising at least one spacer that completely separates each of the at least two channels from one another such that the at least two channels never cross, thereby preventing cross-contamination between the at least two channels; and
   wherein the at least one coagulation assay is measured by optical interrogation at a specific wavelength by an optical source, wherein the specific wavelength is in a range of from about 750 nanometers to about 1,000 nanometers.

2. The coagulation device of claim 1, wherein the patient's liquid test sample is selected from the group consisting of whole blood, plasma, and combinations thereof.

3. The coagulation device of claim 2, wherein the patient's liquid test sample comprises a volume of about 15 microliters.

4. The coagulation device of claim 1, wherein the top section, bottom section, and center section are constructed of materials selected from the group consisting of acrylic, polystyrene, styrene-acrylonitrile, polycarbonate, polyethylene terephthalate, and combinations thereof.

5. The coagulation device of claim 1, wherein each of the at least two channels further comprises a vent.

6. The coagulation device of claim 1, wherein the top portion of the bottom section comprises the at least one coagulation assay reagent.

7. The coagulation device of claim 1, wherein the at least one coagulation assay reagent is selected from the group consisting of thromboplastin, celite, silica, glass, kaolin, ellagic acid, kininogen, prekallikrein, fabric, synthetic plastic, and combination thereof.

8. The coagulation device of claim 1, wherein the optical source is selected from the group consisting of a spectrophotometer, fluorometer, and nephelometer.

9. The coagulation device of claim 1, wherein the specific wavelength is in a range of from 750 nanometers to 850 nanometers.

10. A method for measuring the coagulation characteristics associated with a patient's liquid test sample, the method comprising the steps of:

obtaining a patient's liquid test sample;
introducing the patient's liquid test sample into a coagulation device, the coagulation device comprising:
- a top section, the top section comprising at least one side, a top portion, a bottom portion, and a sample receptacle;
- a bottom section, the bottom section comprising at least one side, a top portion, and a bottom portion;
- a center section, the center section comprising at least one side, a top portion, and a bottom portion, the center section being disposed between the top section and the bottom section, the center section further comprising at least two channels, wherein each of the at least two channels comprises an opening in fluid communication with the sample receptacle a that receives a patient's liquid test sample upon introduction into the coagulation device, further wherein each of the at least two channels is open to the top portion of the bottom section and each of the at least two channels comprises a sample window containing at least one coagulation assay reagent for conducting at least one coagulation assay in each of the at least two channels, the center section further comprising at least one spacer that completely separates each of the at least two channels from one another such that the at least two channels never cross, thereby preventing cross-contamination between the at least two channels;

reacting the patient's liquid test sample with the at least one coagulation assay reagent within each sample window of each of the at least two channels to thereby form a reacted sample;

interrogating the reacted sample within each optical window of the at least two channels with a specific wavelength of light emitted from an optical source, the interrogation occurring over a particular duration of time at predetermined intervals;

measuring the reacted sample to determine a plurality of coagulation characteristics associated with the reacted sample.

11. The method of claim 10, wherein the patient's liquid test sample is selected from the group consisting of whole blood, plasma, and combinations thereof.

12. The method of claim 11, wherein the patient's liquid test sample comprises a volume of about 15 microliters.

13. The method of claim 10, wherein the top section, bottom section, and center section of the coagulation device are constructed of materials selected from the group consisting of acrylic, polystyrene, styrene-acrylonitrile, polycarbonate, polyethylene terephthalate, and combinations thereof.

14. The method of claim 10, wherein each of the at least two channels of the center section further comprises a vent.

15. The method of claim 10, wherein the top portion of the bottom section comprises the at least one coagulation assay reagent.

16. The method of claim 10, wherein the at least one coagulation assay reagent is selected from the group consisting of thrombopastin, celite, silica, glass, kaolin, ellagic acid, kininogen, prekallikrein, fabric, synthetic plastic, and combination thereof.

17. The method of claim 10, the optical source is selected from the group consisting of a spectrophotometer, fluorometer, and nephelometer.

18. The method of claim 17, the specific wavelength is selected from a range of wavelengths selected from the group consisting of 750 nanometers to 850 nanometers.

19. The method of claim 10, wherein the plurality of coagulation characteristics associated with the reacted sample is selected from the group consisting of PT, PTT, aPTT, and combinations thereof.

* * * * *